United States Patent [19]

Kaffka et al.

[11] Patent Number: 4,575,244
[45] Date of Patent: Mar. 11, 1986

[54] DETECTOR SYSTEM FOR MEASURING THE INTENSITY OF A RADIATION SCATTERED AT A PREDETERMINED ANGLE FROM A SAMPLE IRRADIATED AT A SPECIFIED ANGLE OF INCIDENCE

[75] Inventors: Károly Kaffka; Béla Nadai; András Czabaffy; Loránd Horváth, all of Budapest, Hungary

[73] Assignee: Kozponti Elelmiszeripari Kutato Intezet, Budapest, Hungary

[21] Appl. No.: 496,250

[22] Filed: May 19, 1983

[30] Foreign Application Priority Data

May 28, 1982 [HU] Hungary .............................. 1733/82

[51] Int. Cl.$^4$ ........................................... G01N 21/00
[52] U.S. Cl. ..................................................... 356/343
[58] Field of Search ............... 356/340, 337, 343, 237, 356/338; 350/628, 616, 630; 250/238, 352

[56] References Cited

U.S. PATENT DOCUMENTS 3,431,423  3/1969  Keller ................................. 356/338
3,600,581  9/1971  Menke ............................... 250/238
4,360,275 11/1982  Louderback ....................... 350/630

FOREIGN PATENT DOCUMENTS 608644   1/1935  Fed. Rep. of Germany ...... 350/525
55-70732 5/1980  Japan ................................. 356/338
2042166  1/1979  United Kingdom ............... 356/343

OTHER PUBLICATIONS

"Reliable Cooling: A Major Problem is Being Solved by the IR Industry", Missiles & Rockets, 11/9/59, pp. 20–24, La Fond.
Journal Sci. Instrum. 1965, vol. 42, pp. 385–389, "An Infra-Red Reflectometer with a Spheroidal Mirror", by W. R. Blevin and W. J. Brown.
Journal Opt. Soc. Am. 1952, vol. 42, No. 4, pp. 263–265, "A Reflectometer for Measuring Diffuse Reflectance in the Visible and Infrared Regions" by W. J. Derksen & T. I. Monahan.

Primary Examiner—John E. Kittle
Assistant Examiner—Thomas Saitta
Attorney, Agent, or Firm—Young & Thompson

[57] ABSTRACT

The invention relates to a detector system for measuring the intensity of a radiation scattered at a predetermined angle from a sample (10) irradiated at a specified angle of incidence. The detector system comprises a path to transmit an incident beam of radiation onto the sample (10) and at least one radiation sensor (15,16,17,18; 35,36, ... ; 45) positioned in the path of the radiations scattered from the sample (10). According to the invention the detector system has a dome positioned in the path of the radiation scattered from the sample (10). The dome is provided with at least one concave reflecting surface (11,12,13,14; 31,32, ... ; 41) located in a range corresponding to the predetermined scattering angle, and the or each concave reflecting surface forms the image of the sample (10) onto a radiation sensor (15,16,17,18; 35,36, ... ; 45). For example a 0°/45° detector system is preferably arranged so that in the middle of the dome an opening (19) is provided suitable to let the incident beam of radiation fall onto the sample (10), and the dome is provided with at least two concave reflecting surfaces (11,12,13,14; 31,32, ... ) located symmetrically with respect to the sample (10). A 45°/0° detector system can be accomplished so that the dome is a member (44) provided with a rotationally symmetrical concave reflecting surface (41) positioned opposite the sample (10), radiation sensor (45) is disposed at the tip of said concave reflecting surface (41), and in the path of the incident beam there are an outside reflecting surface of revolution (42) of that member (44) as well as a further reflecting surface of revolution (43), the latter reflecting the beam of radiation coming from said outside reflecting surface (42) onto the sample (10) at the specified angle of incidence (FIG. 1).

23 Claims, 4 Drawing Figures

DETECTOR SYSTEM FOR MEASURING THE INTENSITY OF A RADIATION SCATTERED AT A PREDETERMINED ANGLE FROM A SAMPLE IRRADIATED AT A SPECIFIED ANGLE OF INCIDENCE

The subject matter of the present invention is a detector system to measure the intensity of a radiation scattered at a predetermined angle from a sample irradiated at a specified angle of incidence.

BACKGROUND ART

Spectrophotometers for analyzing the composition of materials have been widely known wherein the sample to be tested is illuminated with a monochromatic radiation of variable wavelength at a standard 0° or 45° angle of incidence, and the intensity of the radiation scattered from the sample at an angle of 45° or 0°, respectively, is measured. The standard lay outs of 0°/45° and 45°/0° are intended to eliminate the measuring of the "mirrored" radiation reflected normally from the surface of the sample and ensure the measuring of the "scattered" radiation, only. A common feature of the known devices is that only a small fraction of the radiation scattered back from the sample at the required angle reaches the sensor, as the solid state sensors generally used are usually made with small dimensions and flat sensitive surface because of technological reasons.

This holds true even to a greater extent in case of some samples to be tested, such as grain milling products, fodder blends, meat products, mashed fruits and vegetables, etc., which are more or less inhomogeneous and therefore large exposed surface of the sample to be tested and correspondingly large cross-sectional area of the illuminating radiation should be provided for. From these large sample surfaces even a smaller fraction of the radiation scattered symmetrically in all directions at a predetermined angle with respect to the normal of the sample surface will reach the radiation sensor in the devices known heretofore. In order to utilize at the sensitive surface of the sensor as large a portion of the radiation scattered from the sample at a predetermined angle as possible, several radiation sensors are applied. Thereby the energy reaching the sensitive surface of the sensors can be increased but the density of the radiating energy will remain small, this latter fact being unfavourable considering measuring accuracy. The lower the density of the radiating energy, the smaller the signal provided by the sensor will be, and thus the signal to noise ratio will deteriorate and the time-constant of the sensor will increase.

DISCLOSURE OF THE INVENTION

To eliminate the imperfections described above the object of the present invention is to provide a solution whereby the radiation scattered from the surface of the sample at a predetermined angle can be utilized with a maximum efficiency i.e. the radiation scattered from the surface of the sample at a predetermined angle is directed to the radiation-sensitive surface as completely as possible.

Thus the present invention relates to a detector system for measuring the intensity of a radiation scattered at a predetermined angle from a sample irradiated at a specified angle of incidence, said detector system comprising a path to transmit an incident beam of radiation onto the sample and at least one radiation sensor positioned in the path of the radiation scattered from the sample at the predetermined angle. The invention is characterized by comprising a dome positioned in the path of the radiation scattered from the sample at the predetermined angle, said dome being provided with at least one concave reflecting surface located in a range corresponding to the predetermined scattering angle, the or each concave reflecting surface forming the image of the sample onto a radiation sensor.

In the detector system according to the present invention it is possible and preferable to cover the range corresponding to the predetermined scattering angle completely with said one or more concave reflecting surface.

According to the present invention the radiation scattered from the sample in an entire imaginary hemisphere at a predetermined angle is collected by the properly positioned one or more reflective surfaces onto the sensitive surface of one or more radiation sensors which on the one hand improves the output signal to noise ratio of the sensor(s), and on the other hand increases the sensitivity of the detection. The present invention is particularly preferable for testing materials of inhomogeneous surface as a sample of large surface area can also be applied. The collection of the light scattered in all directions at the predetermined angle is advantageous also where the reflection or transmission factor of the sample at a predetermined angle is non-uniform in different directions, as in this case the detector system according to the present invention provides a measurement result averaged over all directions.

In a preferred embodiment of the present invention an opening is provided in the middle of the dome suitable to let the incident beam of radiation fall onto the sample, and the dome is provided with at least two concave reflecting surfaces positioned symmetrically with respect to the sample. As for the dome, relatively small dimensions can be attained with this embodiment suitable for reflection and transmission measurements as well. In a particularly preferred embodiment of the present invention the detector system is arranged so that the path of the incident beam of radiation and the dome with the radiation sensors attached to it can be fixed in either of two positions with respect to each other, where in one of said positions for reflection measurements the path of the incident beam is provided by the opening formed in the middle of the dome, while in the other position for transmission measurements the path of the incident beam is provided on a side of the sample opposite the dome. In case of transmission measurements the opening formed in the middle of the dome shall be preferably closed with a cover. The detector system suitable for the two different kinds of measurements can be simply realized by supporting the dome rotatably through an angle of 180° around a shaft perpendicular to the axis of the incident beam. Thus in one position of the dome a reflection scattering measurement, in the other position rotated through an angle of 180° a transmission scattering measurement can be effected.

The detector system can be realized with favourable dimensions when the dome is provided with four concave reflecting surfaces arranged symmetrically with respect to the sample. Technologically it is preferable to form the concave reflecting surfaces as spherical surfaces symmetrically arranged around the sample, with their center points lying on a circle concentric with the center of the sample. The radiation detectors may be positioned with their sensitive surface substantially parallel to or substantially perpendicular to the surface of the sample to be tested. It is very advantageous to set up the concave reflecting surfaces and the radiation sensors so that the reduced image of the sample shall be formed onto the sensors, as the density of the radiated energy will then be high at the sensitive surface of the sensors.

The detector system according to the present invention is expediently provided with suitable means to cool the dome and keep its temperature at a constant value, preferably realized with Peltier-elements, in order to decrease the adverse temperature radiation. The surface inside the dome, with the exception of the concave reflecting surfaces, are blackened to decrease the adverse reflected radiation.

In a further embodiment of the detector system according to the present invention, the dome is a member provided with a rotationally symmetric concave reflection surface positioned opposite the surface of the sample, the radiation sensor is disposed at the tip of said concave reflecting surface, and in the path of the incident beam of radiation there are an outside reflective surface of revolution of the member as well as a further reflecting surface of revolution, said further reflecting surface of revolution reflecting the beam of radiation reflected coming from said outside reflecting surface onto the sample at the specified angle of incidence. With this embodiment a measuring arrangement of 45°/0° can be accomplished, with which the sample is exposed to the radiation from all directions at an angle of incidence of 45°, thereby the measuring of the radiation scattered from the sample at an angle of 0° results in a value averaged for the total radiation reaching the sample from all directions.

BRIEF DESCRIPTION OF THE DRAWINGS

The invention will be described in the following on the basis of preferred embodiments illustrated in the accompanying drawings, wherein.

MODES FOR CARRYING OUT THE INVENTION

The same or similar members are denoted with the same reference number throughout the drawings.

Figure 1:
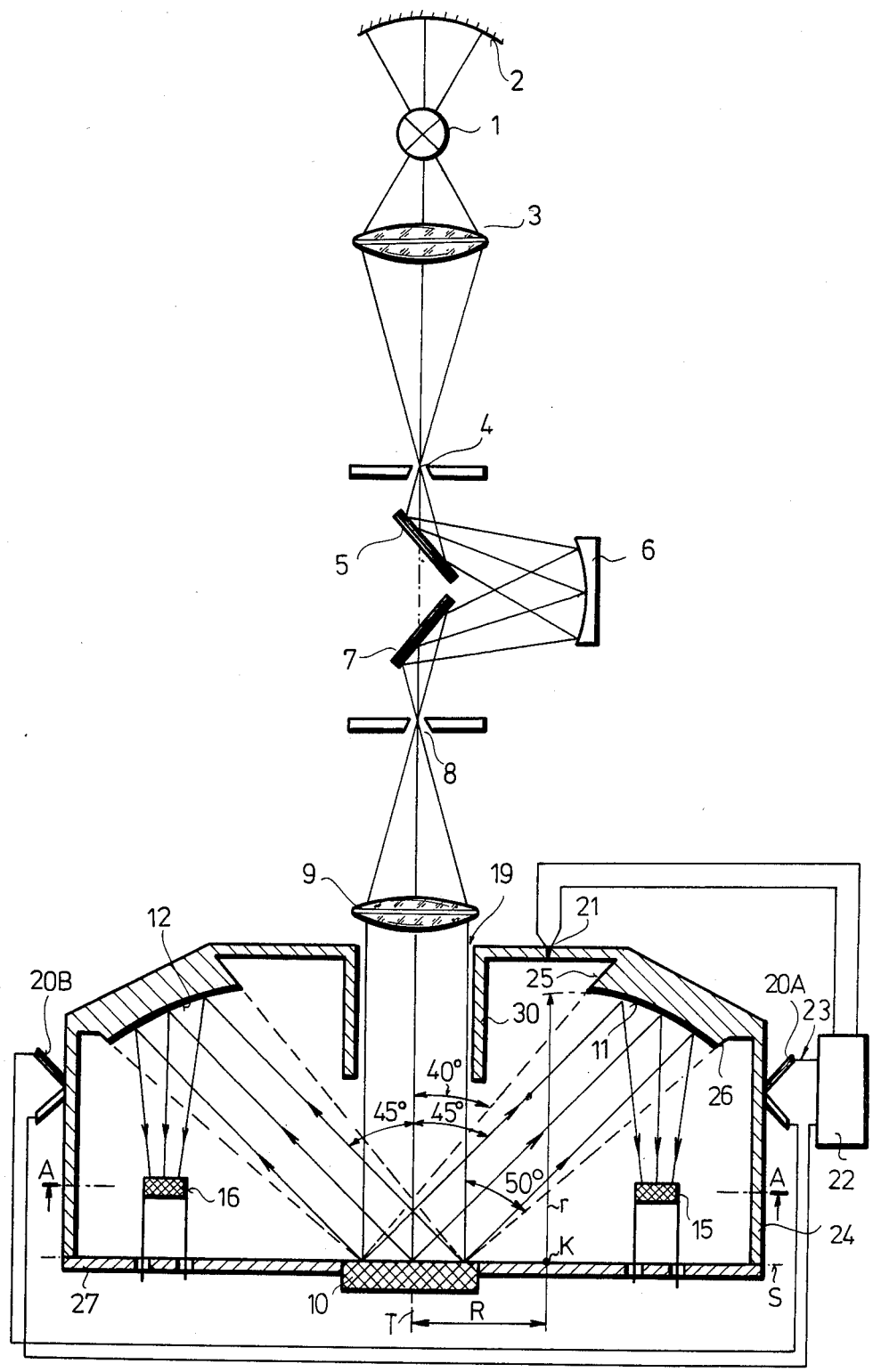
FIG. 1 is a schematic drawing of a spectrophotometer comprising an embodiment of the detector system according to the invention, featured by an angle of incidence of 0° and an angle of scattering of 45°, partly as a sectional view taken along the line B—B of FIG. 2.
Figure 2:
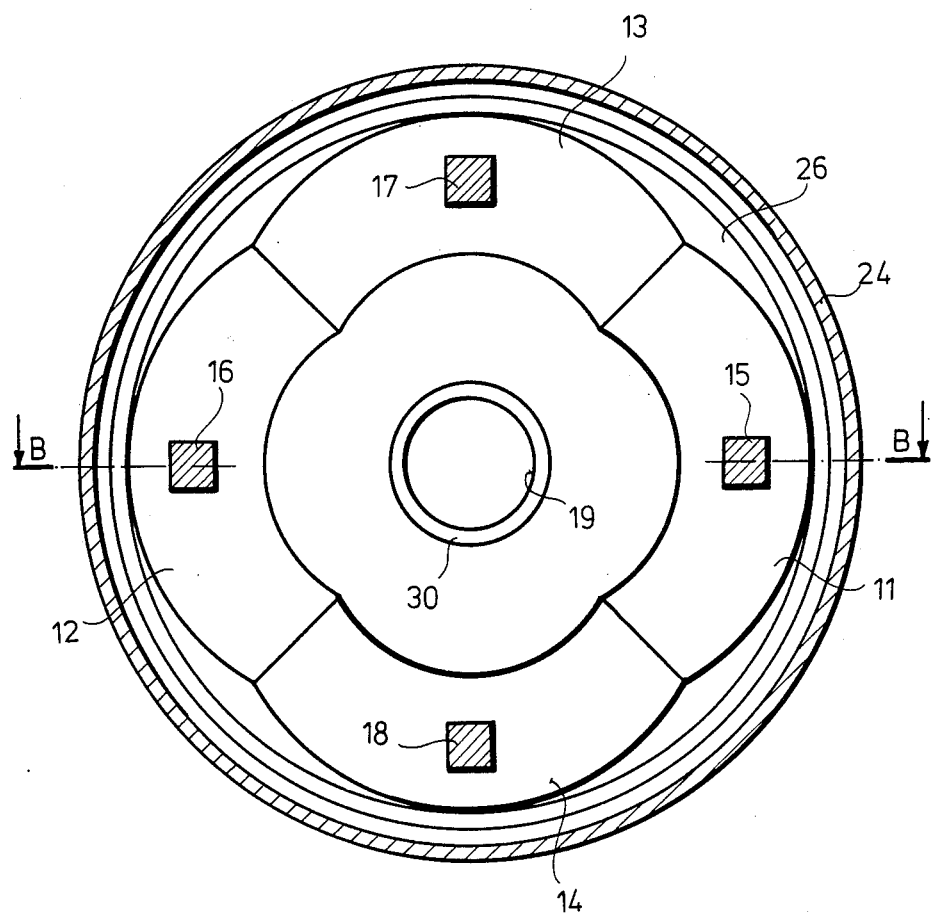
FIG. 2 is a sectional view of the detector system illustrated in FIG. 1, taken along the line A—A.

In the spectrophotometer illustrated in FIGS. 1 and 2 the polychromatic radiation emitted directly by a source 1 and reflected also by a concave mirror 2 is imaged by a lens 3 onto an entrance slit 4. The beam of radiation passing through the entrance slit 4 is reflected by a flat mirror 5 onto a concave reflection grating 6 and from that the monochromatic radiation is transmitted via a flat mirror 7 and an exit slit 8 onto a collimator lens 9. The optical system from the entrance slit 4 to exit slit 8 represents a monochromator. The parallel beam of radiation emerging from the collimator lens 9 forms the incident beam falling on a sample 10 at an angle of 0° with respect to the normal in a detector system according to the present invention. The sample 10 is positioned in the middle of a circular baseplate 27, symmetrically to the axis T of the beam. A housing 24 is mounted to the baseplate 27, said housing 24 having a dome in which a circular opening 19 for the incident beam and concave reflecting surfaces 11, 12, 13 and 14 are formed, in the embodiment shown four spherical surfaces of radius r and center point K, where the center points K are located along a circle of radius R being concentric with the center of the sample 10. The concave reflecting surfaces 11, 12, 13 and 14 are shaped so that the radiation scattered even from the extreme points of the sample 10 at an angle of 45°−5° and 45°+5° should be imaged onto radiation sensors 15, 16, 17 and 18, respectively. The range of the scattering angle can be limited for example by confining the concave reflecting surfaces 11, 12, 13 and 14 within an inner conical surface 25 and an outer conical surface 26. The concave reflecting surfaces 11, 12, 13 and 14 are shaped and located so that the reduced image of the sample 10 should be formed on the radiation sensors 15, 16, 17 and 18 mounted to the baseplate 27 with their sensitive surface disposed parallel to and above the surface of the sample 10. The radiation sensors 15, 16, 17 and 18 should be selected in accordance with the wavelength of the radiation to be measured. Application of solid state radiation sensors is preferred, where the outputs can be connected in parallel.

As it can clearly be seen in FIG. 2, the concave reflecting surfaces 11, 12, 13 and 14 cover completely the 45°±5° range of angles concentrically, thereby the total radiation scattered in the predetermined direction is projected onto the radiation sensors 15, 16, 17 and 18. Around the axis T of the dome at the circular opening 19 provided for the incident beam a cylindrical portion 30 is formed to prevent the radiation sensors 15, 16, 17 and 18 from being be exposed to the effect of the direct radiation transmitted through the opening 19. As it can be seen in FIG. 2, the number of the concave reflecting surfaces 11, 12, 13 and 14 as well as their shape have to be selected so that the lines of intersections lie completely outside the cylindrical portion 30 bounding the incident beam of radiation.

The baseplate 27, the housing 24 and the inside surface of the dome with the exception of the concave reflecting surfaces 11, 12, 13 and 14 are all blackened in order to decrease the effect of the adverse reflected radiation on the sensors 15, 16, 17 and 18. The adverse temperature radiation is decreased by a thermostat 23 cooling and keeping the temperature of the housing 24 and the dome as well constant, comprising a thermocouple 21 fitted in the wall of the dome or housing 24, serially connected Peltier-elements, e.g. two of them, 20 A and 20 B located symmterically to the axis T and attached to the outside surface of the housing 24, and a temperature controller 22.

The embodiment illustrated in FIG. 1 is intended for measuring the radiation scattered from the surface of the sample 10. However, the detector system is applicable for transmission measurements, too, where a fraction of the radiation scattered at an angle of 45° is to be measured after falling on the sample at an incident angle of 0° and transmitting through the sample. Such a transmission measurement can be accomplished for example by setting a flat mirror in place of the sample 10 illustrated in FIG. 1 and positioning the sample to be tested onto this mirror. Another possible arrangement for transmission measurements can be accomplished by positioning the baseplate 27 and the housing 24, together with the sample 10 and the radiation sensors 15, 16, 17 and 18 attached to it, symmetrically to the plane S, for example by rotating the complete assembly through an angle of 180° around a shaft coincident with line A—A and intersecting the axis T. With this arrangement of the detector system the opening 19 is preferably closed with a cover not shown. The same transmission arrangement can also be effected by displacing the optical system producing the incident beam of radiation in such a manner that the incident beam falls on the sample 10 from below in FIG. 1, at a 0° angle of incidence. Thereby the detector system provided by the present invention can be set up suitably for reflection and transmission measurements as well.

Figure 3:
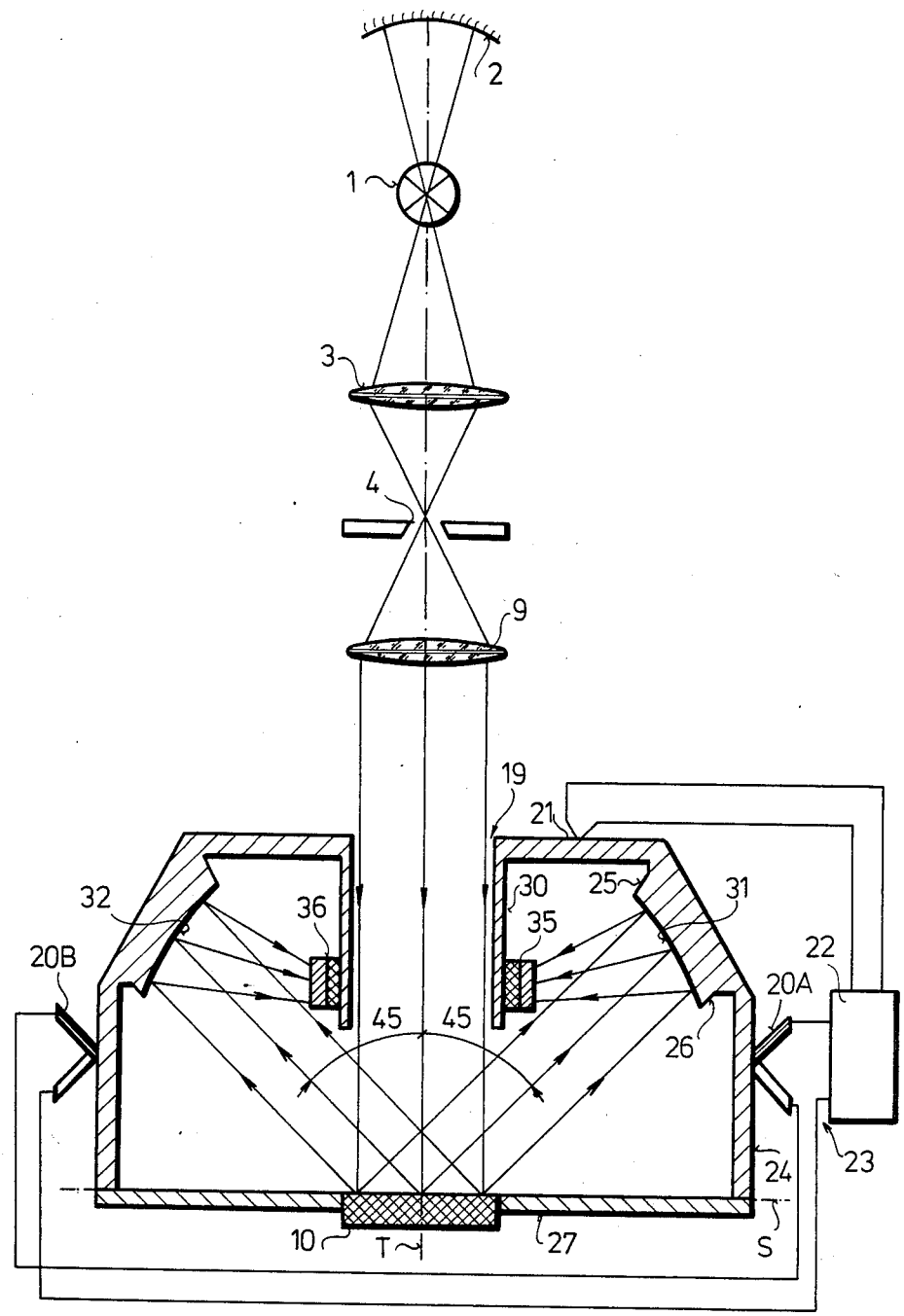
FIG. 3 is a schematic drawing of a photometer comprising an embodiment of the detector system according to the invention, featured by an angle of incidence of 0° and an angle of scattering of 45°, partly as a sectional view.

With the photometer shown in FIG. 3 the radiation emitted directly by the source 1 and reflected by the concave mirror 2 is imaged by the lens 3 onto the entrance slit 4. The beam of radiation passing through the entrance slit 4 is collimated by a lens 9, this parallel beam of radiation being the incident beam for the detector system, falling on the sample 10 at a 0° angle of incidence. The detector system illustrated in FIG. 3 differs from that of FIG. 1 in the position of the radiation sensors, in so far as the four radiation detectors, two of them denoted by 35 and 36 being illustrated only, are mounted to the cylindrical portion 30 with their sensitive surface substantially perpendicular to the surface of the sample 10. The four concave reflecting surfaces 31, 32, . . . , e.g. spherical surfaces, have to be shaped correspondingly. In FIG. 3 the detector system according to the present invention is utilized in a photometer with which the radiation scattered from the sample 10 at an angle of 45° can be measured and compared to the radiation scattered at the same angle from a reference material positioned in the place of the sample 10. This arrangement is also suitable for transmission measurements as it was described in connection with FIGS. 1 and 2.

Figure 4:
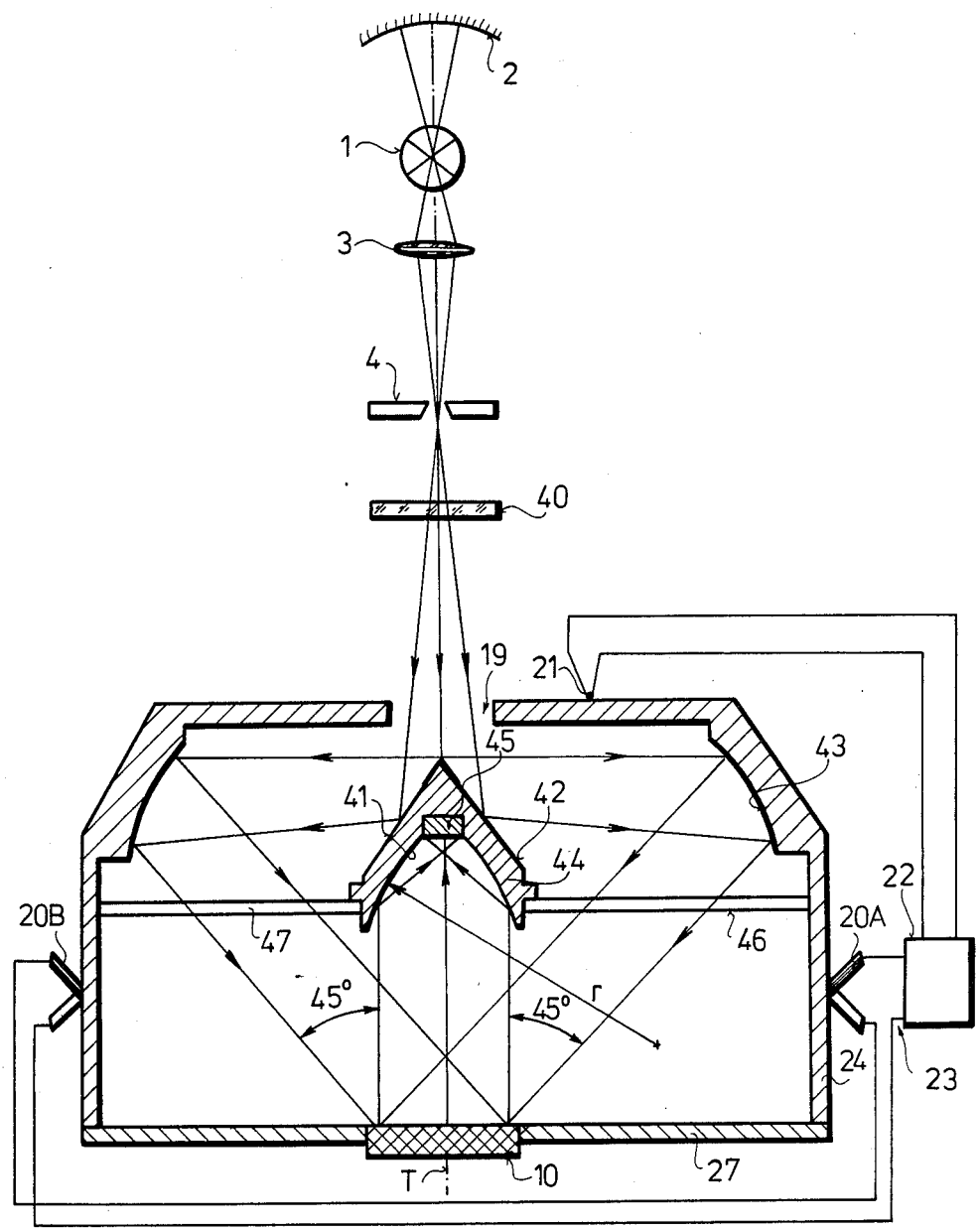
FIG. 4 is a schematic drawing of a spectrophotometer comprising an embodiment of the detector system according to the invention, featured by an angle of incidence of 45° and an angle of scattering of 0°, partly as a sectional view.

In a spectrophotometer shown in FIG. 4 an embodiment of the detector system according to the present invention can be seen where the incident beam falls on the sample 10 at an angle of incidence of 45° and the radiation scattered at an angle of 0° is to be measured. The polychromatic radiation emitted directly by the source 1 and reflected also by the concave mirror 2 is transmitted through an interchangeable filter 40 via a lens 3 and an entrance slit 4, then passing through the opening 19 reaches a conical reflecting surface of revolution 42 being symmetrical to the axis T of a member 44. The member 44 is attached to the housing 24 by means of thin ribs 46 and 47. The divergent beam of radiation is reflected by the surface of revolution 42 as a rotationally symmetrical divergent beam onto a concave reflecting surface of revolution 43, the generatrix of which may be e.g. a circular arc, and finally a rotationally symmetrical parallel beam is reflected onto the sample 10 at an angle of incidence of 45°. The radiation scattered back from the sample 10 at an angle of 0° reaches an inner concave reflecting surface 41 of the member 44, the generatrix of which may be e.g. a circular arc, reflecting the radiation onto a single radiation sensor 45. The radiation sensor 45 is attached to the member 44 at the tip of the rotationally symmetrical concave reflecting surface 41.

The embodiment of FIG. 4 can also be accomplished by collimating the beam of radiation by means of a lens located following the filter 40, then a parallel beam is transmitted through the opening 19, and accordingly the reflecting surface of revolution 43 has to be formed conically. A further embodiment can also be accomplished where both the reflecting surface of revolution 42 and the reflecting surface of revolution 43 are of curved section and selected so that the parallel or nonparallel beam of radiation transmitted through the opening 19 be formed as a rotationally symmetrical parallel beam falling on the sample 10 at an angle of incidence of 45°.

With the detector system illustrated in FIG. 4 a transmission measurement can be effected by setting a flat mirror in place of the sample 10 and positioning the sample to be tested onto this mirror.

We claim:

1. A detector system for measuring the intensity of a radiation scattered from a sample irradiated by an incident beam of radiation, said detector system comprising
   means defining a path to transmit the incident beam of radiation onto the sample substantially at a specified angle of incidence,
   an optical arrangement having at least two substantially contiguous concave reflecting surfaces, each said surface being located in the path of only the radiation scattered from the sample in a small range about a predetermined angle in particular section of an imagninary hemisphere, said concave reflecting surfaces covering substantially the whole said imaginary hemisphere in said range,
   a plurality of radiation sensors one for each of said concave reflecting surfaces, each of said concave reflecting surfaces focusing the radiation scattered from the sample in said particular section onto the radiation sensor associated with it.

2. The detector system according to claim 1, and a housing in which said radiation sensors are located, said housing having a dome provided with said concave reflecting surfaces at its inner surface and a baseplate for positioning the sample, said concave reflecting surfaces being arranged symmetrically in relation to the sample.

3. The detector system according to claim 2, wherein said dome comprises an opening surrounded by said concave reflecting surfaces to let the incident beam of radiation fall onto the sample at an angle of incidence of substantially 0° with respect to the normal.

4. The detector system according to claim 3, wherein said path of the incident beam of radiation and said housing together with the radiation sensors and the sample are arranged to be fixed in either of two different positions in relation to each other, in one of said positions for reflection scattering measurements the path of the incident beam of radiation being provided on one side of the sample by said opening, whereas in the other of said positions for transmission scattering measurements the path of the incident beam of radiation being provided on the other side of the sample and said opening being closed by a cover.

5. The detector system according to claim 4 wherein said housing together with said radiation sensors and the sample is supported rotatably through an angle of 180° around a shaft perpendicular to the axis of the incident beam of radiation.

6. The detector system according to claim 2 wherein said dome comprises at its inner surface four concave reflecting surfaces arranged symmetrically in relation to the sample, and, in the interior of said housing, four radiation sensors.

7. The detector system according to claim 1 wherein said concave reflecting surfaces and said radiation sensors are positioned in such a manner that a reduced image of the sample is formed on each radiation sensor.

8. The detector system according to claim 2 wherein said radiation sensors are located beside the sample so that their sensing surfaces are substantially parallel to the surface of the sample.

9. The detector system according to claim 3 wherein said dome has a cylindrical portion extending inwardly at the opening, and said radiation sensors are mounted to said cylindrical portion so that their sensing surfaces are substantially perpendicular to the surface of the sample.

10. The detector system according to claim 2 wherein said housing comprises a thermostat device for cooling it and keeping its temperature at a constant value.

11. The detector system according to claim 10 wherein said thermostat device comprises Peltier-elements attached to said housing as cooling means.

12. The detector system according to claim 2 wherein all inner surfaces of said housing with the exception of said concave reflecting surfaces are blackened.

13. The detector system according to claim 1 wherein the incidence angle of the beam falling onto the sample is 0°±5° and said concave reflecting surfaces are located in a range corresponding to a scattering angle of 45°±5° in relation to the normal of the surface of the sample.

14. The detector system according to claim 10 wherein said radiation sensors are solid-state devices.

15. The detector system according to claim 14 wherein said solid-state radiation sensors are connected at their outputs in parallel.

16. A detector system for measuring the intensity of a radiation scattered at a predetermined angle from a sample irradiated at a specified angle of incidence, said detector system comprising
means defining a path to transmit an incident beam of radiation onto the sample at the specified angle of incidence,
at least two radiation sensors for detecting the radiation scattered from the sample,
a dome being provided with at least two concave reflecting surfaces located symmetrically in relation to the sample in a range corresponding to the predetermined scattering angle, each of said concave reflecting surfaces forming the image of the sample onto one of said radiation sensors, said dome being provided with an opening formed in the middle of it to let the incident beam of radiation fall onto the sample, said concave reflecting surfaces having their lines of intersections lying outside the boundary surface of the incident beam of radiation transmitted through said opening.

17. A detector system for measuring the intensity of a radiation scattered at a predetermined angle from a sample irradiated at a specified angle of incidence, said detector system comprising
means defining a path to transmit an incident beam of radiation onto the sample at the specified angle of incidence,
at least two radiation sensors for detecting the radiation scattered from the sample,
a dome having at least two concave reflecting surfaces located in a range corresponding to the predetermined scattering angle, each of said concave reflecting surfaces forming the image of the sample onto one of said radiation sensors, said concave reflecting surfaces being spherical surfaces located symmetrically in relation to the sample with their center points lying equidistant from the center of the sample along a circle.

18. A detector system for measuring the intensity of a radiation scattered from a sample irradiated by an incident beam of radiation, said detector system comprising
means defining a path to transmit the incident beam of radiation onto the sample substantially at a specified angle of incidence,
a member provided with an inner rotationally symmetrical concave reflecting surface positioned opposite the surface of the sample and located only in the path of the radiation scattered from the sample in a small range around 0°,
a radiation sensor disposed at the tip of said concave reflecting surface so that said concave reflecting surface focuses the radiation scattered from the sample in said range onto said radiation sensor, said path of the incident beam of radiation comprising an outer reflecting surface of revolution of said member and a further reflecting surface of revolution, the latter reflecting the beam of radiation coming from said outer reflecting surface of revolution onto the sample in a small range around the specified angle of incidence in an entire imaginary hemisphere.

19. The detector system according to claim 18, and a housing in which said member with said radiation sensor is centrally located, said housing having a dome and a baseplate for positioning the sample, said dome being provided with said further reflecting surface of revolution at its inner surface and with an opening surrounded by said further reflecting surface of revolution to let the incoming beam of radiation fall onto said outer reflecting surface of revolution of said member.

20. The detector system according to claim 18 wherein said further reflecting surface of revolution is arranged to reflect the beam of radiation onto the sample at an angle of incidence of 45°±5°.

21. The detector system according to claim 19 wherein said housing comprises a thermostat device for cooling it and keeping its temperature at a constant value.

22. The detector system according to claim 21 wherein said thermostat device comprises Peliter-elements attached to said housing as cooling means.

23. The detector system according to claim 21 wherein said radiation sensor is a solid-state device.

* * * * *